United States Patent [19]
Belanger, et al.

[11] 4,454,325
[45] Jun. 12, 1984

[54] N-(ALKENYL)-2-AZA-2'-HYDROXY-5,6-BENZOTRICYCLO[6.3.0$^{1,8}$.0$^{4,11}$] UNDECANES

[75] Inventors: Patrice C. Belanger, Dollard des Ormeaux; Robert N. Young, Senneville, both of Canada

[73] Assignee: Merck Sharp & Dohme I.A. Corp., Rahway, N.J.

[21] Appl. No.: 453,662

[22] Filed: Dec. 27, 1982

Related U.S. Application Data

[62] Division of Ser. No. 228,482, Jan. 26, 1981, Pat. No. 4,376,779.

[51] Int. Cl.$^3$ ............................................ C07D 209/94
[52] U.S. Cl. ...................................... 548/425; 424/274
[58] Field of Search ........................................ 548/425

[56] References Cited
U.S. PATENT DOCUMENTS
4,376,779 3/1983 Belanger et al. .................... 548/424

*Primary Examiner*—Paul M. Coughlan, Jr.
*Assistant Examiner*—D. B. Springer
*Attorney, Agent, or Firm*—Theresa Y. Cheng; Mario A. Monaco

[57] ABSTRACT

Novel N-(substituted) derivatives of 2-aza-2'-hydroxy-5,6-benzotricyclo[6.3.0$^{1,8}$.0$^{4,11}$] undecane of the formula:

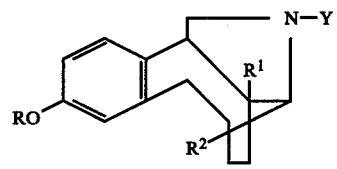

are centrally acting analgesics effective in the relief of pain.

4 Claims, No Drawings

N-(ALKENYL)-2-AZA-2'-HYDROXY-5,6-BENZO-TRICYCLO[6.3.0$^{1,8}$.0$^{4,11}$] UNDECANES

This is a division of application Ser. No. 228,482, filed Jan. 26, 1981 and issued Mar. 15, 1983 to U.S. Pat. No. 4,376,779.

BACKGROUND OF THE INVENTION

1. Field of the Invention

The present invention is concerned with novel centrally-acting analgesic agents, i.e., agents acting on opiate receptors within the central nervous system to produce potent and profound analgesia.

The most widely used centrally-acting analgesic continues to be morphine. This drug, however, has serious drawbacks as the result of certain pronounced side effects. Not only does use or morphine usually lead to physiological and psychological dependency, but morphine is a respiratory depressant as well.

Thus, there has been a continuous search for a centrally-acting analgesic with the potency of morphine, but without its dangerous side effects. For example, many analgesic agents based on the morphine model have been prepared. One of the best known of these is meperidine. While this drug was originally thought to be non-addicting, it was soon found to have dangerous addiction liability.

Other centrally-acting analgesics include the class of compounds known as the benzomorphans. Pentazocine, phenazocine, cyclazocine, ketocyclazocine, and ethylketocycloazocine are some of the better known members of this class of compounds. However, as with other centrally-acting analgesics developed heretofore, the benzomorphans also have undesirable addiction qualities.

2. Brief Description of the Prior Art

Robinson et. al., U.S. Pat. Nos. 3,700,734; 3,514,463; 3,513,169; and 3,499,906 describe benzomorphan derivatives having analgesic activity.

Freed et. al., U.S. Pat. Nos. 3,836,670; 4,001,331; and 4,076,953 describe benzobicycloalkane amines for inducing analgesia.

Co-pending U.S. Ser. No. 117,701, filed Feb. 19, 1980, describes derivatives of 2-hydroxy-6,9-methano-11-amino-5,6,7,8,9,10-hexahydrobenzocyclooctene.

However, none of the compounds disclosed in any of the above would suggest the novel compounds of the present invention to a person of ordinary skill in the art.

SUMMARY OF THE INVENTION

The present invention relates to novel N-(substituted) derivatives of 2-aza-2'-hydroxy-5,6-benzotricyclo[6.3.0$^{1,8}$.0$^{4,11}$] undecane and pharmaceutically acceptable salts thereof.

The present invention also relates to a method of treating pain comprising administering to a patient (human or animal) in need of such treatment, a therapeutically effective amount of a novel compound of the present invention; as well as to a pharmaceutical composition for use in treating pain comprising a pharmaceutically acceptable carrier and a therapeutically effective amount of a novel compound of the present invention.

The present invention also relates to a method of preparing the novel compounds of the present invention, as well as to novel intermediates useful in said method.

The novel compounds of the present invention may be represented by the following formula:

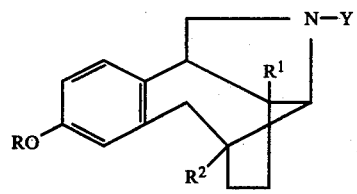

where
R is hydrogen or methyl;
R$^1$, and R$^2$, are each independently hydrogen or C$_{1-4}$ alkyl; and
Y is (a) C$_{1-4}$alkyl; (b) C$_{1-4}$alkenyl; (c) C$_{3-4}$cycloalkylmethyl; (d) phenyl C$_{1-4}$alkyl; or (e)

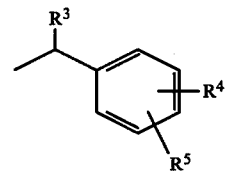

wherein:
R$^3$ is hydrogen or C$_{1-4}$alkyl; and
R$^4$ and R$^5$ are each independently selected from the group consisting of (1) hydrogen; (2) halo; (3) C$_{1-4}$ alkyl; (4) C$_{1-4}$ alkoxy; (5) amino, and mono- and di-C$_{1-4}$ alkyl substituted amino; (6) cyano; (7) trifluoromethyl; (8) trifluoromethylthio; (9) C$_{1-4}$ alkylthio; (10) C$_{1-4}$ alkylsulfoxide; (11) C$_{1-4}$ alkylsulfone; (12) hydroxy; and (13) phenyl;

and a pharmaceutically acceptable salt thereof.

The numbering of the 2-aza-2'-hydroxy-5,6-benzotricyclo[6.3.0$^{1,8}$.0$^{4,11}$] undecane compounds of the present invention is illustrated below:

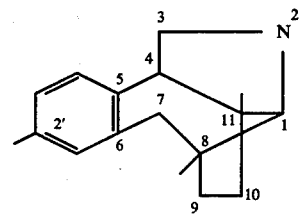

Included in this invention are the optical isomers of the compounds of Formula I, which may vary to some extent in their biological activity. Carbon atoms 1 and 4 are asymmetric.

These isomers can be separated into their optical isomers [dextro (+) and levo (−)] by preparing the diastereoisomeric salts with optically active acids, either D (+) or L (−), which salts can then be separated by conventional methods such as fractional crystallization. Thus, it is to be understood that included in this invention, in addition to racemic mixtures of the novel N-(substituted)-2-aza-2'-hydroxy-5,6-benzotricyclo[6.3.0$^{1,8}$.0$^{4,11}$]undecane compounds, are the individual optical isomers, i.e., the dextrorotatory (+) and levorotatory (−) isomers of said novel compounds.

Among the novel compounds of the present invention, certain compounds are preferred. For example, the N-(substituted-benzy) compounds are preferred, and the phenyl moiety substituents, $R_4$ and $R^5$, are preferred in the following order: para, meta, ortho, and it is preferred that there be only one such substituent. The most preferred substituents, in order of preference, are: methoxy, chloro, dimethylamine, hydrogen, and methyl.

It is preferred that the $R^1$, $R^2$, and $R^3$ substituents be hydrogen.

Representative compounds of the present invention are the following:

N-(4-chlorobenzyl)-2-aza-2'-hydroxy-5,6-benzotricyclo-[6.3.0$^{1,8}$.0$^{4,11}$] undecane;
N-(4-methoxybenzyl)-2-aza-2'-hydroxy-5,6-benzotricyclo-[6.3.0$^{1,8}$.0$^{4,11}$] undecane;
N-(4-dimethylaminobenzyl)-2-aza-2'-hydroxy-5,6-benzotricyclo-[6.3.0$^{1,8}$.0$^{4,11}$] undecane;
N-(4-phenylbenzyl)-2-aza-2'-hydroxy-5,6-benzotricyclo-[6.3.0$^{1,8}$.0$^{4,11}$] undecane;
N-(4-fluorobenzyl)-2-aza-2'-hydroxy-5,6-benzotricyclo-[6.3.0$^{1,8}$.0$^{4,11}$] undecane;
N-(3-methoxybenzyl)-2-aza-2'-hydroxy-5,6-benzotricyclo-[6.3.0$^{1,8}$.0$^{4,11}$] undecane;
N-(3-hydroxybenzyl)-2-aza-2'-hydroxy-5,6-benzotricyclo-[6.3.0$^{1,8}$.0$^{4,11}$] undecane;
N-methyl-2-aza-2'-hydroxy-5,6-benzotricyclo[6.3.0$^{1,8}$.0$^{4,11}$]undecane;
N-allyl-2-aza-2'-hydroxy-5,6-benzotricyclo[6.3.0$^{1,8}$.0$^{4,11}$]undecane;
N-phenethyl-2-aza-2'-hydroxy-5,6-benzotricyclo[6.3.0$^{1,8}$.0$^{4,11}$]undecane.

Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Water or oil-soluble or dispersible products are thereby obtained.

The novel compounds of the present invention are useful in alleviating pain in animal and human patients. For example, compounds of Formula I show good activity in a modified Randall Selitto test. Good activity in this test is accepted in the art as indicative of useful analgesic activity.

In addition, the compounds of the present invention show a reduction in the severity of the serious side effects associated with members of the morphine family of naturally occurring alkaloidal analgesics, such as addiction, tolerance, and respiratory depression. Moreover, unlike the morphine analgesics, the compounds of the present invention are orally active.

Various tests in animals have been carried out to show the ability of the compounds of this invention to exhibit reactions that can be correlated with activity in humans. One such test, outlined by Winter and Flataker in *J. Phar. Exp. Tera.*, 150, 1, pp. 165-171, shows the ability of the compounds of Formula I to exhibit analgesic effect. Measurements are made of the reaction threshold to pressure in the hind paws of rats injected with a phlogistic agent. These are compared with known analgesic drugs, and marked increased effects can be found. Drug dosages of up to 64 mg/kg are administered by the subcutaneous route. The experiments are carried out on Sprague-Dawley female rats weighing from 60 to 80 grams. The response threshold is determined by applying pressure to the foot and reading on a manometer the pressure at which an audible "squeak" is elicited. Groups of ten rats are used for each test and the average reading is recorded.

Thus, the novel compounds of Formula I possess a high degree of analgesic activity, and are, accordingly, useful in treating animal and human patients experiencing moderate to severe pain originating from any one of a number of different sources.

The novel compounds of Formula I are also useful as anti-diarrheal and anti-tussive agents.

For these purposes the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium, carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcelluslose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the analgesic agents are employed.

Dosage levels of the order of 5 to 50 mg per day are useful in the treatment of the above indicated conditions. For example, analgesic activity is manifested by the administration of from about 0.1 to 1.0 milligrams of the compound per kilogram of body weight per day. Advantageously from about 0.05 mg to about 0.5 mg per kilogram of body weight per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 to 50 mg of active agent compounded with an appropriate and convenient amount of carrier material which may vary from about 5 to about 95 percent of the total composition. Dosage unit forms will generally contain between from about 2 mg to about 15 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The novel compounds of Formula I are conveniently prepared by the following methods from known starting materials.

The starting materials are 5,6,7,8,9,10-hexahydro-6,9-methanobenzocyclooctene-11-ones and are readily prepared by the reaction of $\alpha,\alpha'$-dihalo xylene or an appropriately substituted xylene and a cyclic ketone derivative. Thus, for example, reaction of $\alpha,\alpha'$-dibromo xylene and the pyrrolidine enamine of cyclopentanone or cyclohexanone in an aprotic solvent such as acetonitrile produces the desired 6,9-methanobenzocyclooctene-11-one or the corresponding benzocyclononen-11-one. In order to introduce the phenolic hydroxyl group into the cyclooctene-11-one compounds in a one-step reaction, the starting ketone is treated in strongly acid solution, preferably in trifluoroacetic acid, with thallium trifluoroacetate at a temperature of from 0°–50° C. and preferably between 10°–30° C. The reaction is allowed to proceed for a period of friom 1–24 hours and is then treated with an oxidizing agent, as for example lead tetraacetate, and the resulting mixture is then stirred with heating, preferably at reflux temperature of the reaction mixture for a period of from 1–5 hours. The entire rection mixture is then treated with triphenyl phosphine in order to free the hydroxy cyclooctene-11-one from its complex, and then the desired ketone purified by removal of the reaction solvent by evaporation under reduced pressure followed by extraction of the residual material with chloroform, and the chloroform extract washed with water and dried to yield the desired product, which is conveniently purified by crystallization from a solvent.

The phenolic hydroxyl compound prepared as just described can then be converted to the corresponding methoxy compound by reaction with a methylating agent such as dimethylsulfate or methyl iodide in the presence of a base such as potassium carbonate.

The hydroxy and methoxy 11-keto compounds prepared according to the previous procedure are readily converted to the corresponding 11-amino compounds by conversion to the corresponding oximes, followed by catalytic reduction to the amine. Thus, for example, D,L-5,6,7,8,9,10-hexahydro-2-hydroxy-6,9-methanobenzocyclooctene-11-one is converted to the corresponding 11-oximino compound by refluxing in the presence of an approximately equimolar amount of hydroxylamine hydrochloride. Following formation of the oxime, the reaction mixture is diluted with water and extracted to isolate the oxime, which is then further purified by chromatography on silica gel, followed by elution with chloroform containing traces of methanol. The oxime thus isolated is reduced, for example with hydrogen in the presence of a catalyst such as platinum oxide, to give the 11-amino compound, which is then purified by chromatography.

Once the 11-amino compounds are prepared, they become starting materials for a sequence of reactions which may be illustrated as follows:

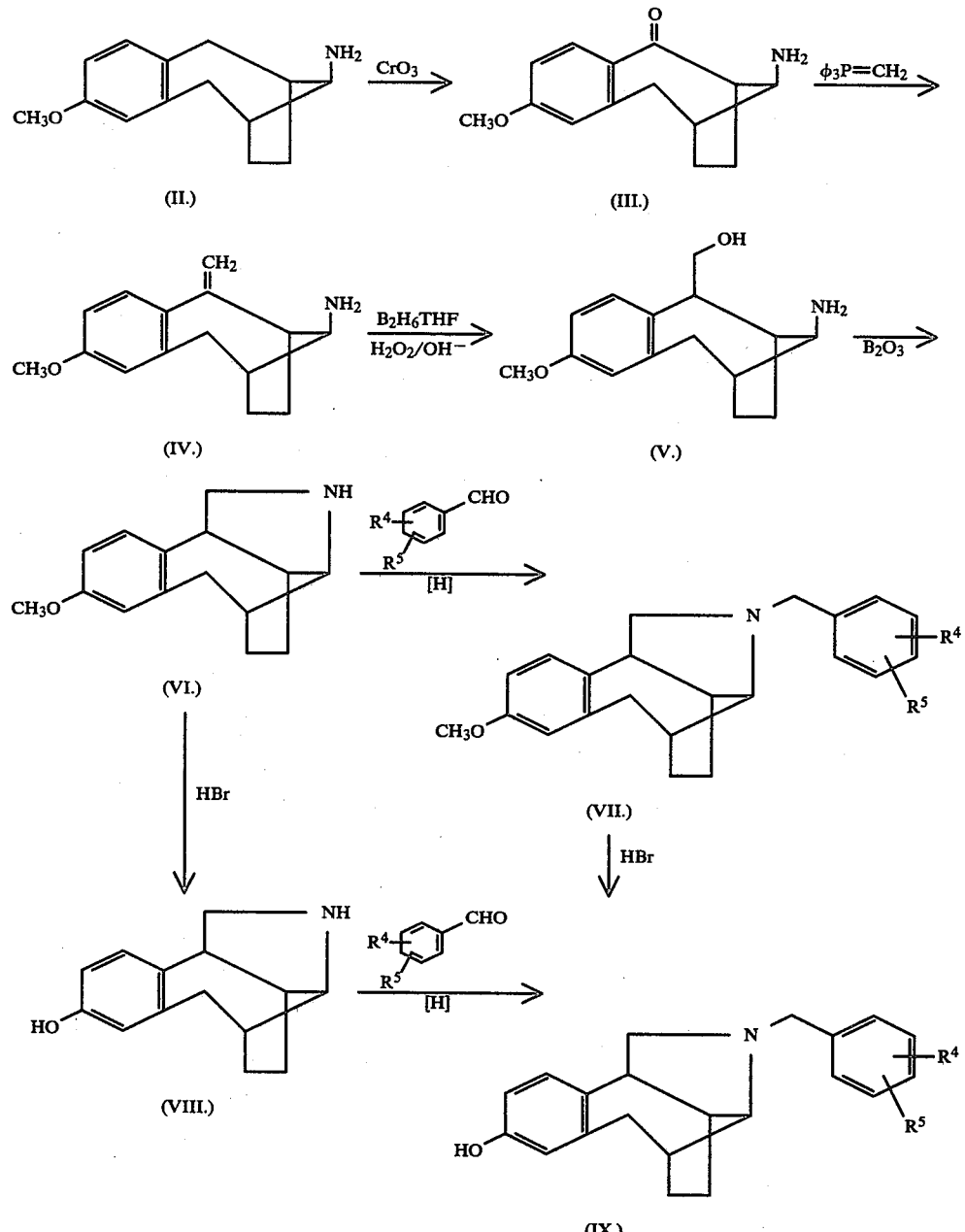

A. In the first reaction, the amine (II) is oxidized with a suitable oxidizing agent, such as chromium trioxide, to produce the 5-oxo compound (III). Where chromium trioxide is used, the reaction is carried out in the presence of concentrated sulfuric acid with steam-bath heating for at least two hours. The reaction mixture is neutralized and the product separates with cooling.

B. In the second reaction, the 5-oxo compound (III) is treated with methyl triphenyl phosphonium bromide in the presence of n-butyl lithium at 0° C., with slow temperature increase to reflux where heating is maintained for at least 30 minutes. The resulting 5-methylene compound (IV) is separated by extraction, for example with ethyl acetate and chloroform.

C. In the third reaction, the 5-methylene compound (IV) is first treated with diborane in a suitable solvent, for example tetrahydrofuran, under an inert atmosphere, preferably argon, and then with water followed by sodium hydroxide and hydrogen peroxide. The resulting 5-hydroxymethyl compound (V) is separated by conventional means.

D. In the fourth reaction, ring closure is accomplished by treating the 5-hydroxymethyl compound (V) with boron trioxide in a suitable solvent such as diglyme under an inert atmosphere, preferably argon, with heating at reflux for about 40 hours. The resulting 2-aza-2'-methoxy-5,6-benzotricyclo-[6.3.0$^{1,8}$,0$^{4,11}$] undecane (VI) is separated by extraction.

E. The 2'-methoxy-benzotricyclo compound (VI) may be converted to the corresponding 2'-hydroxy compound (VIII) by treatment with hydrobromic acid in the presence of acetic acid under an inert atmosphere such as argon, heating at reflux for about 30 hours. The product may be separated by chromatography. This same process may be used to prepare a 2'-hydroxy compound of the present invention (IX) from the corresponding 2'-methoxy compound of the present invention (VII), whose preparation is described below.

F. Conversion of compound (VI) to compound (VII) and of compound (VIII) to compound (IX) may be accomplished by following one of the following three procedures:

the unsubstituted ring compound (VI) or (VIII) is treated with:
(a) the appropriately substituted benzaldehyde:
 (1) in the presence of sodium cyanoborohydride using methanol as solvent; or
 (2) in the presence of platinum oxide under a hydrogen atmosphere using ethanol as solvent; or with:
(b) the appropriately substituted benzyl halide in the presence of diisopropylamine using acetonitrile as solvent; to give the N-benzyl compounds (VII) and (IX).

The compounds of the present invention wherein Y is $C_{1-4}$alkyl, $C_{1-4}$alkenyl, $C_{3-4}$cycloalkylmethyl and phenyl $C_{1-4}$alkyl may be prepared by essentially the same process described above in F.(b), substituting for the benzyl halide an equivalent amount of the appropriate halide, for example, methyl iodide, allyl bromide, or phenethyl bromide.

A process for the preparation of the compounds of the present invention which are substituted by alkyl substituents, e.g., methyl substituents in the 8 and/or 11 positions, begins with the treatment of an α,α-dihaloxylene with an alkylated or dialkylated derivative of the appropriate cycloalkanone-enamine. Thus, for example, α,α-dibromoxylene is treated with the pyrrolidine enamine of 2,5-dimethylcyclopentanone to produce the corresponding 6,9-dimethyl-5,6,7,8,9,10-hexahydro-6,9-methanobenzocyclooctene-11-one, followed by thallation as described hereinabove, to introduce the corresponding 2'-hydroxy compound and subsequent conversion to the oxime, followed by catalytic reduction to the desired d,1-11-endo-amino-6,9-dimethyl-5,6,7,8,9,10-hexahydro-6,9-methanobenzocyclooctene.

The novel intermediates of the present invention are the compound produced by ring closure (VI): 2-aza-2'-methoxy-5,6-benzotricyclo[6.3.0$^{1,8}$,0$^{4,11}$] undecane; and the corresponding 2'-hydroxy compound (VIII) prepared by hydrolysis of the 2'-methoxy compound as described above: 2-aza-2'-hydroxy-5,6-benzotricyclo[6.3.0$^{1,8}$,0$^{4,11}$]undecane.

The following examples illustrate preparation of various of the novel compounds of the present invention, but are not intended to in any way be a limitation thereof.

EXAMPLE 1

D,L-N-(4-Methoxybenzyl)-2-aza-2'-hydroxy-5,6-benzotricyclo[6.3.0$^{1,8}$,0$^{4,11}$] undecane hydrochloride Step A. D,L-Endo-amino-2-methoxy-5-oxo-5,6,7,8,9,10-hexahydro-6,9-methanobenzocyclooctene A solution of chromium trioxide (5.2 g; 52 mmoles) in a mixture of concentrated sulfuric acid (18 ml) and water (200 ml) is added to a solution of D,L-endo-11-amino-2-methoxy-5,6,7,8,9,10-hexahydro-6,9-methanobenzocyclooctene (10 g; 39 mmoles) in a mixture of concentrated sulfuric acid (18 ml) and water (200 ml). The mixture is heated on a steam-bath for 3 hours. It is then cooled in an ice bath and concentrated ammonia is added slowly to adjust the pH to 8. The mixture is shaken with ethyl acetate (300 ml) and filtered through celite. The precipitate is washed with ethyl acetate (200 ml). The filtrate is decanted and the organic layer is washed with brine, dried over sodium sulfate and concentrated to an oil. Purification by column chromatography eluting with chloroform, methanol, and methanol saturated with ammonia-100:2.5:0.5 (v:v:v) yields D,L-endo-11-amino-2-methoxy-5-oxo-5,6,7,8,9,10-hexahydro-6,9-methanobenzocyclooctene (5.4 g; 59%). Recrystallization from ethyl acetate:hexane, it melts at 96°–97° C.

The hydrochloride, recrystallized from ethyl acetate:ether melts at 213°–215° C.

Elemental analysis for $C_{14}N_{17}NO_2 \cdot HCl$; Calculated: %C, 62.53; %H, 6.89; %N, 5.11; %Cl, 13.42; Found: %C, 62.80; %H, 6.78; %N, 5.23; %Cl, 13.26.

Step B. D,L-Endo-11-amino-2-methoxy-5-methylene-5,6,7,8,9,10-hexahydro-6,9-methanobenzocyclooctene To a suspension of methyl triphenyl phosphonium bromide (22.25 g; 62.3 mmoles) in dioxane under nitrogen maintained at 0° C., butyl lithium (2.2M in hexane) is added dropwise until the yellow color persists for a minute. Then, n-butyl lithium (28 ml; 62 mmoles) is added and the reaction mixture is stirred at room temperature for 20 minutes.

D,L-endo-11-amino-2-methoxy-5-oxo-5,6,7,8,9,10-hexahydro-6,9-methanobenzocyclooctene (7.1 g; 30.7 mmoles) is then added at 0° C. The reaction mixture is allowed to attain room temperature and is heated under reflux for 30 minutes.

The mixture is poured onto ice and extracted with ethyl acetate (2×200 ml) and with chloroform (200 ml). The combined extracts are washed with brine and dried over sodium sulfate. Evaporation of the solvent leaves a gum which is purified by column chromatography, eluting with chloroform, methanol, ammonium hydroxide (95:5:0.5; v:v:v) to yield D,L-endo-11-amino-2-methoxy-5-methylene-5,6,7,8,9,10-hexahydro-6,9-methanobenzocyclooctene (3.94 g; 56%), m.p. 61°–63° C.

The hydrochloride salt melts at 229°–230° C.

Elemental analysis for $C_{15}H_{19}NO.HCl.1/2H_2O$: Calculated: %C, 65.56; %H, 7.70; %N, 5.10; %Cl, 12.90: Found: %C, 65.83; %H, 7.52; %N, 5.04; %Cl, 13.01.

Step C. D,L-Endo-11-amino-2-methoxy-5-hydroxymethyl-5,6,7,8,9,10-hexahydro-6,9-methanobenzocyclooctene D,L-endo-11-amino-2-methoxy-5-methylene-5,6,7,8,9,10-hexahydro-6,9-methanobenzocyclooctene (11.2 g; 48.9 mmoles) in dry tetrahydrofuran is treated at 0° C. under argon with 1M diborane in tetrahydrofuran (117 ml). The mixture is stirred at room temperature for 2 hours. It is cooled at 0° C. and is treated carefully with water (47 ml), then with 6N sodium hydroxide (29.5 ml) and with 30% hydroden peroxide (23.5 ml). The mixture is stirred for 15 minutes at 0° C. and 30 minutes at room temperature. Excess peroxide is destroyed with sodium bisulfite (4.7 g) and more 6N sodium hydroxide is added before extracting the mixture with chloroform (3×140 ml). The organic phase is washed with brine, dried over sodium sulfate, and evaporated to a gum. This is taken up in methanol (140 ml) and 5N ethanolic hydrogen chloride is added. The mixture is refluxed for 30 minutes and evaporated. The residue is evaporated twice with methanol and the residual gum crystallized from ethyl acetate to yield D,L-endo-11-amino-2-methoxy-5-hydroxymethyl-5,6,7,8,9,10-hexahydro-6,9-methanobenzocyclooctene (8.7 g; 63%) melting point: 219°–220° C.

Elemental analysis for $C_{15}H_{21}NO_2.HCl$: Calculated: %C, 63.48; %H, 7.81; %N, 4.94; %Cl, 12.49: Found: %C, 63.36; %H, 8.07; %N, 4.81; %Cl, 12.81.

Step D. D,L-Aza-2'-methoxy-5,6-benzotriclo[6.3.0$^{1,8}$.0$^{4,11}$] undecane

D,L-endo-11-amino-2-methoxy-5-hydroxymethyl-5,6,7,8,9,10-hexahydro-6,9-methanobenzocyclooctene (2.5 g; 8.8 mmoles), boron trioxide (739 mg; 10.6 mmoles) and diglyme (15 ml) are refluxed under argon for 40 hours. The diglyme is removed under vacuum. The solid is treated with hydrogen chloride in methanol and the mixture is heated under reflux for 30 minutes. The volatiles are removed under vacuum to yield a solid foam. This is treated with methylene chloride and basified with 6N sodium hydroxide. The aqueous layer is extracted again with methylene chloride. The combined extracts are dried over potassium carbonate and evaporated to an oil (1.95 g; 97%). D,L-2-aza-2'-methoxy-5,6-benzotriclo[6.3.0$^{1,8}$.0$^{4,11}$] undecane is characterized as the phosphate salt, melting point: 245°–250° C. (dec).

Elemental analysis for $C_{15}H_{19}NO.H_3PO_4$: Calculated: %C, 55.04; %H, 6.77; %N, 4.28; %P, 9.66: Found: %C, 55.02; %H, 6.67; %N, 4.22; %P, 10.05.

Step E. D,L-2-Aza-2'-hydroxy-5,6-benzotriclo[6.3.0$^{1,8}$.0$^{4,11}$] undecane

D,L-2-aza-2'-hydroxy-5,6-benzotriclo[6.3.0$^{1,8}$.0$^{4,11}$]undecane (2.68 g; 11.7 mmoles) is refluxed under argon in a mixture of acetic acid (67 ml) and 47% hydrobromic acid (677 ml) for 50 hours. The mixture is evaporated to dryness. The residue is dissolved in hot methanol and evaporated onto 15 g silica gel which is then placed on top of 80 g silica gel. Elution with chloroform:methanol:ammonium hydroxide (100:15:1 v:v:v) yields D,L-2-aza-2'-hydroxy-5,6-benzotriclo[6.3.0$^{1,8}$.0$^{4,11}$] undecane hydrobromide: 2.23 g; 89%; melting point: 284°–286° C.

Elemental analysis for $C_{14}H_{17}NO.HBr$: Calculated: %C, 56.77; %H, 6.12; %N, 4.73: Found: %C, 56.85; %H, 6.34; %N, 4.66.

Step F. D,L-N-(4-Methoxybenzyl)-2-aza-2'-hydroxy-5,6-benzotricyclo[6.3.0$^{1,8}$.0$^{4,11}$] undecane hydrochloride D,L-2-Aza-2'-hydroxy-5,6-benzotriclo[6.3.0$^{1,8}$.0$^{4,11}$] undecane (782 mg; 3.64 mmole) and p-methoxybenzaldehyde (544 mg; 4.0 mmole) are stirred in ethanol (25 ml) solution for 0.5 hour, after which the reaction mixture is hydrogenated in the presence of platinum oxide (30 mg). The mixture is then filtered, evaporated to an oil, and the oil is dissolved in acetone (5 ml) and ethanol (2.5 ml). Excess ethanolic hydrogen chloride is added, after which a solid begins to crystallize. Crude product of 915 mg (67.8%) is obtained, m.p. 237°–238° C. (dec). Purification on silica gel plates using 95:5:0.5 chloroform/methanol/ammonium hydroxide, followed by conversion to the hydrochloride salt gives 119 mg of product (8.8%), m.p. 234°–236° C. (dec)

Elemental analysis for $C_{22}H_{25}NO_2.HCl.1/2H_2O$: Calculated: %C, 69.37; %H, 7.14; %N, 3.68; %Cl, 9.31: Found: %C, 69.84; %H, 7.08; %N, 3.58; %Cl, 9.03.

EXAMPLES 2–6

Following the procedures in Example 1, Step F and substituting for the p-methoxybenzaldehyde used therein, an equivalent amount of the appropriately substituted benzaldehyde; and, where indicated below, substituting for the D,L-2-aza-2'-hydroxy-5,6-benzotricyclo[6.3.0$^{1,8}$.0$^{4,11}$] undecane starting material, the corresponding 2'-methoxy benzotriclo compound prepared in Step D above, and subsequently treating with hydrobromic acid and acetic acid as described in Example 7, Step B below, there are prepared the following compounds of the present invention:

| EXP. NO. | $R^4, R^5$ | STARTING MATERIAL | MELTING POINT °C. | (salt) | ELEMENTAL ANALYSIS |
|---|---|---|---|---|---|
| 2 | 4-NMe$_2$ | 2'-hydroxy | 235–245 | (HCl) | C: 65.55  H: 7.18  N: 6.65  Cl: 16.83 |
|   |   |   |   |   | C: 65.21  H: 7.46  N: 6.47  Cl: 17.02 |
| 3 | 4-C$_6$H$_5$ | 2'-hydroxy | 242–7 | (HCl) | C: 74.38  H: 6.94  N: 3.21  Cl: 8.13 |
|   |   |   |   |   | C: 74.48  H: 6.68  N: 3.24  Cl: 7.76 |
| 4 | 4-F | 2'-methoxy | 253–4 | (HBr) | C: 62.38  H: 5.73  N: 3.46  Cl: 19.76 |
|   |   |   |   |   | C: 62.36  H: 5.83  N: 3.43  Cl: 19.92 |
| 5 | 3-OCH$_3$ | 2'-methoxy | 155 | (HCl) | C: 71.05  H: 7.05  N: 3.79  Cl: 9.53 |
|   |   |   |   |   | C: 70.75  H: 7.57  N: 3.49  Cl: 9.62 |
| 6 | 3-OH | 2'-methoxy | 257–261 | (HCl) | C: 69.70  H: 6.68  N: 3.87  Cl: 9.80 |
|   |   |   |   |   | C: 69.70  H: 6.91  N: 3.67  Cl: 9.86 |

EXAMPLE 7

D,L-N-(4-Chlorobenzyl)-2-aza-2'-hydroxy-5,6-benzotricyclo[6.3.0$^{1,8}$.0$^{4,11}$] undecane hydrobromide Step A. D,L-N-(4-Chlorobenzyl)-2-aza-2'-methoxy-5,6-benzotricyclo[6.3.0$^{1,8}$.0$^{4,11}$] undecane D,L-2-Aza-2'-methoxy-5,6-benzotricyclo-[6.3.0$^{1,8}$.0$^{4,11}$] undecane (1.25 g; 5.46 mmole); p-chlorobenzyl chloride (923 mg, 5.73 mmole); acetonitrile (15 ml); and diisopropylethylamine (5 ml) are mixed and allowed to stand at room temperature for 24 hours, and the course of the reaction is monitored by thin layer chromatography. The solvent is removed by rotary evaporation, and the residue is dissolved in chloroform (25 ml). The solution is shaken with 6N sodium hydroxide (2 ml), and the aqueous layer is extracted with chloroform (2×10 ml). The dried organic extracts are absorbed on silica gel (10 g), and the product is isolated by column chromatography (90 g silica gel eluted with 1% ammonia saturated methanol in chloroform) to give 1.846 g (95.6%).

Step B. D,L-N-(4-Chlorobenzyl)-2-aza-2'-hydroxy-5,6-benzotricyclo[6.3.0$^{1,8}$.0$^{4,11}$] undecane hydrobromide D,L-N-(4-Chlorobenzyl)-2-aza-2'-methoxy-5,6-benzotricyclo[6.3.0$^{1,8}$.0$^{4,11}$] undecane (1.200 g; 3.39 mmoles) is heated under reflux for 5 hours with a mixture of acetic acid (0.5 ml) and concentrated hydrobromic acid (0.5 ml, 47%) in an argon atmosphere. The reaction mixture is combined with a prior reaction mixture obtained using 100 mg of undecane and evaporated to dryness under vacuum, and the resulting brown gum is crystallized from acetone (6 ml). The solid is filtered, washed with 1:1 acetone/ether (6 ml), then with ether, and dried. Product obtained is 858 mg (60.6%)

Elemental analysis fo $C_{21}H_{22}NOCl.HBr$: Calculated: %C, 59.94; %H, 5.51; %N, 3.33; %Br, 18.99: Found: %C, 60.04; %H, 5.57; %N, 3.18; %Br, 18.72.

What is claimed is:

1. A compound of the formula

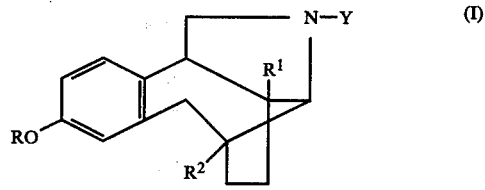

where
R is hydrogen or methyl;
$R^1$ and $R^2$ are each independently hydrogen or $C_{1-4}$alkyl providing that they cannot be simultaneously both t-butyl; and
Y is $C_{3-4}$alkenyl
or a pharmaceutically acceptable acid addition salt thereof.

2. A compound according to claim 1 wherein the compound is N-allyl-2-aza-2'-hydroxy-5,6-benzotricyclo[6.3.0$^{1,8}$.0$^{4,11}$] undecane.

3. The compound 2-aza-2'-methoxy-5,6-benzotricyclo[6.3.0$^{1,8}$.0$^{4,11}$] undecane.

4. The compound 2-aza-2'-hydroxy-5,6-benzotricyclo[6.3.0$^{1,8}$.0$^{4,11}$] undecane.

* * * * *